United States Patent [19]

Ghose

[11] Patent Number: 4,692,411
[45] Date of Patent: Sep. 8, 1987

[54] SEPARATION OF SPECIFIC BIOLOGICAL CELLS BY A BIOCHEMICAL FILTER

[76] Inventor: Rabindra N. Ghose, 8167 Mulholland Ter., Los Angeles, Calif. 90046

[21] Appl. No.: 529,347

[22] Filed: Sep. 6, 1983

[51] Int. Cl.$^4$ .................... C12N 1/00; C12N 1/02; A01N 1/02; C12Q 1/24
[52] U.S. Cl. .................................. 435/243; 435/2; 435/30; 435/261; 435/311; 435/803; 436/824; 604/4; 604/5
[58] Field of Search ............... 435/2, 269, 311, 803, 435/30, 261, 813, 7, 243; 436/519, 523, 824; 604/4, 5; 424/101; 210/927, 196

[56] References Cited

U.S. PATENT DOCUMENTS 4,416,772 11/1983 Sato et al. ..................... 210/266 X
4,465,593 8/1984 Wemhoff ....................... 210/196 X

FOREIGN PATENT DOCUMENTS 83489 7/1983 European Pat. Off. ............ 210/927
3005605 10/1981 Fed. Rep. of Germany ...... 435/261
54-122714 9/1979 Japan ................................. 210/927

Primary Examiner—Robert J. Warden
Assistant Examiner—Shawn P. Foley
Attorney, Agent, or Firm—Rabindra N. Ghose

[57] ABSTRACT

Apparatus and methods for selective removal of specific biological cells or specific antigens or antibodies, from fluid containing their mixture with other biological cells and particulates are described. Filtration by this biochemical filter system is effected in a continuous closed-loop fluid flow path. The apparatus described herein comprises a source of fluid containing specific biological cells, antigens or antibodies to be removed; a source of complementary cells or complementary antibodies for the antigens and complementary antigens for the antibodies which can form large agglutinates following a biochemical reaction a reaction chamber providing conditions favorable for fast clump formation following the reaction; a filter for trapping large agglutinates; one or more pumps to regulate various flow rates; and necessary connecting links to form a closed-loop fluid flow path that includes the sources of biological cells, antigens or antibodies and complementary cells, reaction chamber, and filter chamber.

28 Claims, 3 Drawing Figures

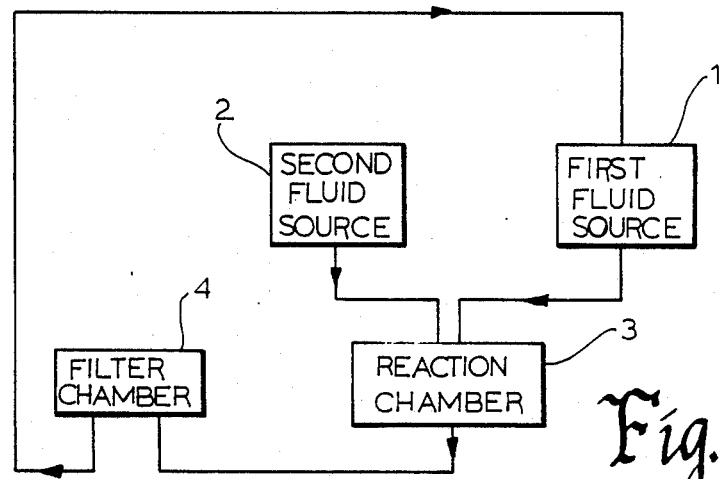
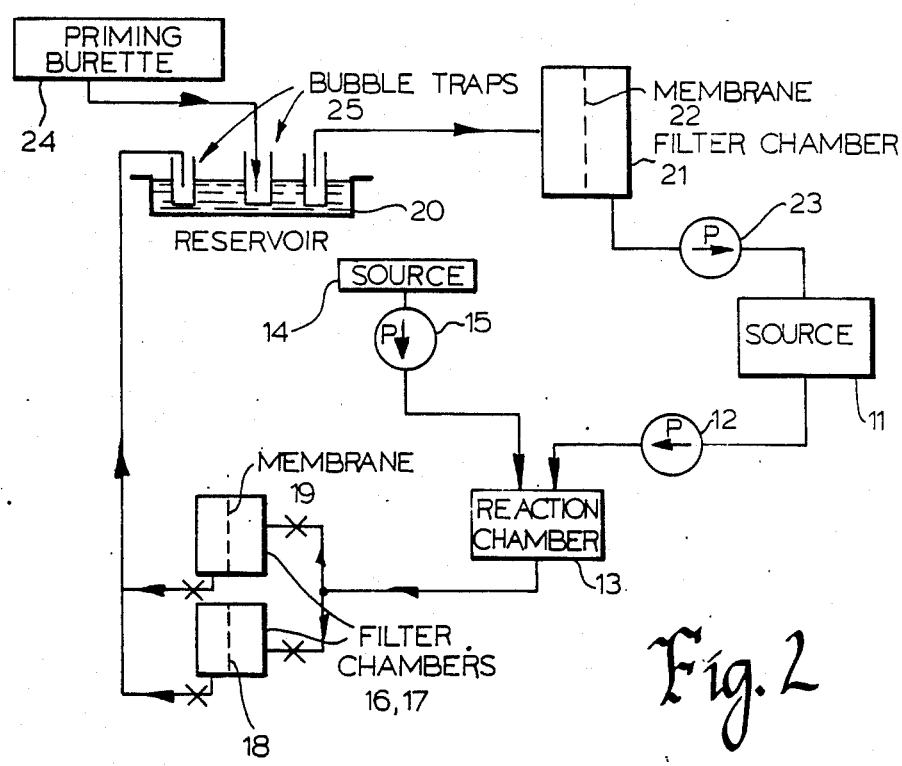

SEPARATION OF SPECIFIC BIOLOGICAL CELLS BY A BIOCHEMICAL FILTER

BACKGROUND OF THE INVENTION

The inventive apparatus and method described herein utilizes the concept of highly selective biochemical reactions between two types of complementary biological cells leading to the formation of large clumps or agglutinates and a separation concept based on different dimensions of the clumps and the biological cells and particulates not involved in the reaction. Antigens and corresponding specific antibodies, for example, are two such types of complementary biological cells, which when reacted, lead to the formation of large agglutinates.

In general, the antigen-antibody reaction occurs in two stages[1]. In the first stage, an individual antigen combines with a complementary antibody. If specific antibodies are selected for a particular type of antigen to be removed or separated from a fluid, such as blood, the first-stage reaction may take place in a fraction of a second. Furthermore, the antibodies will react specifically with antigen cells which are complementary to each other and not with other cells of different species. Numerous papers have been published to demonstrate the extremely selective affinity between specific antibody and antigen cells. This selectivity in reaction is utilized in this invention.

The second stage antigen-antibody reaction involves the formation of large agglutinates or clumps, containing a large and often interconnected chain of antigen-antibody molecules. As early as in 1934, Marrack[2] described the reaction between antigen and antibody cells resulting in precipitation in terms of the building up of aggregates of large sizes. Marrack pointed out that if the antibody has more than one valency, it will be possible for antigens and antibodies to be bound together in the form of a coarse lattice.

The study in the field of second state antigen-antibody reaction leading to precipitation or agglutination was also made long ago by Heidelberger[3] who originally made use of purified capsular polysaccharide of the type III pneumococcus as antigens. The reactions were observed when an increasing amount of antigens were added to a constant amount of antiserum or antibody. After a time, sufficient for the complete reaction to occur, the precipitates were washed free of uncombined reactant and the total antigen content was estimated. It was seen that the amount of antibody precipitate increased to a maximum with the increasing addition of antigen and then suddenly this amount declined so that in the extreme antigen-excess case, no precipitate was formed. For a given antigen and the corresponding complementary antibody, then, there appears to be an optimal proportion of antigen to antibody cells which yield the largest agglutinates.

The second state antigen-antibody reaction is utilized in this invention so that physically large agglutinates or clumps can be obtained. The formation of large clumps of antigen and antibody molecules is believed to result from multiple reactions which can be described as follows:

| | | |
|---|---|---|
| A + S | — | AS |
| AS + A | — | ASA |
| ASA + A | — | ASA |
| ASA + S | — | A ASA AS AS | where A and S denote respectively the antigen and antiserum (antibody) molecules. Indeed other reactions, besides those shown above, are possible.

The formation of large clumps of antigen and antibody has been observed by a large number of researchers. From such observations it appears that the dimensions of the antigen-antibody clump and the rate of clump formation depend on several factors such as antigen-antibody cells ratio, electrolyte concentration of the solution, temperature, antibody valency, etc. A polarizing electromagnetic field[4] and stirring can also affect clump sizes and their formation rates.

The concentration of antigens and antibodies in the solution, perhaps, affect the clump formation mast markedly. It is well known, for example, that the precipitation or agglutination varies in composition according to the proportions of antigen and antibody in the reacting mixture. If antibody is present in excess, the precipitation will contain relatively more of this component and vice versa. It is seen that if the valency of the antigen is N and that of the antibody is 2, there will be increasing chances of building large aggregates up to a point where S/A ratio is about N/2. It may be recognized that this combination of two substances to form a compound of variable composition according to the proportions in which they are mixed has no counterpart in chemical reactions of small molecules, but it is more akin to the polymerization of plastics. It is, of course, essential that the antigen be multivalent and the antibody be at least bivalent for the lattice hypothesis to work in this way.

An application of time-varying electromagnetic field shows possibilities of enhancing the rate of agglutination process. For example, large aggregates of non-spherical dielectric particles including biological cells have been made by the application of a time-varying electromagnetic field. This process is often referred to as pearl-chain formation. The formation of large aggregates of antigen and antibody molecules could be obtained by similar techniques. The pearl-chain formation is regarded as a direct consequence of increasing the free energy of the biological cells in solution by a nonthermal energy source such as the electromagnetic field. Since the energy that can be imparted by an electromagnetic field to the biological cells depends on the coupling mechanism, which in turn depends on the frequency and polarization of the electromagnetic field for a given set of antigens and antibodies, the average time required to form a clump of a given dimension can be considerably reduced if an appropriate electromagnetic field is impressed on the solution.

In addition, adaptation of complement fixation procedures, provisions of stirring and a reduction of hapten concentration in the antibody solution that normally terminates the antigen-antibody chain could be used to increase the agglutination and reduce the time required for the second-stage antigen-antibody reaction.

Besides antibodies, agglutinins have been developed such that clumps can be formed following a highly specific reaction of such agglutinins with certain complementary biological cells in a solution. Burger[5] for example, reported an agglutinin prepared from wheat germ lipase which reacted with tissue culture cell lines that were transformed by a tumor virus, while under identical conditions, their untransformed parent cell lines did not agglutinate. These and similar agglutinins can be used to form clumps and to separate specific biological cells.

Once large clumps containing the biological cells to be removed or separated are formed, a filter, that discriminates the filtrate against the residue based on their grossly different sizes, can be used for the final separation of the cells. Various mechanizations of the selective cell separation or cell removal in a closed-loop fluid flow path, containing the source of fluid, a reaction chamber where clumps of the cells to be removed are formed through a highly specific biochemical reaction, and a filter chamber where the clumps are retained permitting the fluid along with non-reacted cells and particulates to return to the source, are embodied in the invention.

SUMMARY OF THE INVENTION

The invention described herein comprises an apparatus and method for selectively removing specific biological cells from a fluid containing such cells without affecting other cells and particulates also contained in the same fluid. As used herein for ease of understanding, the term 'cells' includes antigens, antibodies and biological cells which represent, in a generic sense, biological substances that form clumps following a biochemical reaction with complementary biological substances. The separation or selective removal of cells is effected by first forming large clumps of the cells to be removed by adding complementary cells which biochemically react almost exclusively with such cells and then filtering the fluid so that the clumps containing the cells to be removed are trapped in the filter. The filtration is effected by discriminating clumps of larger dimensions against other cells and particulates of smaller dimensions, which do not participate in the biochemical reaction. The filtrate, without the clumps, is returned to the original source of the fluid and the filter containing the clumps is removed periodically to complete the separation process. The cell separation or selective cell removal process is conducted in a continuous closed-loop fluid flow path such that the cells which escape the biochemical filtering in one cycle, are subjected to the same filtering process again and again in subsequent cycles, until they are trapped.

When the fluid is blood and its source is a living system, the biochemical filter of the invention described herein may constitute an extracorporeal blood circulatory system where specific antigens, such as specific bacteria, viruses, fungi, or parasites contained in the blood can be selectively removed. For the clump formation, as is essential in this invention, certain quantities of complementary antibodies need to be added to the blood only while it flows through the extra-corporeal blood circulatory system. Such a selective separation of antigens from blood may constitute an alternative form of therapy. The volume of blood flow per unit time in the extra-corporeal blood circulatory system need not be as large as in a kidney dialysis-machine, since, in most cases, the rate of growth of antigens in blood is relatively slow. Thus, if the antigens are removed at a rate faster than their growth rate, the blood could be made almost free of the specific antigens eventually. The process will be similar to that encountered in a swimming pool filter where only a small volume of water is processed in a given period but the rate of processing or filtering is a little faster than the growth rate of the pollutants. One advantage of this form of therapy by a selective removal of specific antigens is that no rejection or side-effects of drugs can occur, since no foreign substances, such as drugs are introduced into the body. Also, unlike in many chemotherapies, where desired cells and tissues in the blood stream can be damaged or destroyed while the undesired cells or antigens are destroyed, the effective therapy through the selective removal of antigens cannot harm the cells and tissues not participating in the highly specific biochemical reaction.

Another advantage of the inventive apparatus and method is that undesired or harmful antibodies in the blood can also be removed selectively by adding complementary antigens in the extra-corporeal blood circulatory system, constituting the biochemical filter.

Still another advantage of the inventive apparatus and method is that some undesired biological cells, such as neoplastic cells, which are neither antigens nor antibodies, but have antigenic affinity for certain complementary cells, can also be removed from the blood.

Another advantage of the inventive apparatus and method is to prevent permeation of cancerous cells into other parts of the body following a tumor-surgery. To achieve this result, one or more units of the inventive apparatus can be inserted into the principal arteries and veins prior to the surgery so that cancerous cells are trapped in the filter while blood with normal cells and tissues join the bloodstream.

Another advantage of the inventive apparatus and method is to complement drugs in therapy, particularly when the growth rate of certain bacteria or viruses is too fast for drugs to provide a remedy in a timely manner. A simultaneous removal of some bacteria or viruses along with the destruction of other bacteria or viruses by drugs may, in some cases, accelerate the theraputic process.

Still another advantage of the inventive apparatus and method is to offer theraputic remedy for certain bacteria and viruses for which no drug exists or is yet invented. It should be noted, however, that the application of the inventive apparatus and method described herein, need not be confined to the removal of antigens or antibodies from the blood.

The reservoir of knowledge of antigen-antibody reactions and the formation of clumps of biological cells when appropriate complementary cells are added, may be regarded as prior art relevant to this invention. The art of extra-corporeal blood circulatory system, as is found in the dialysis-machine, is also well known now and may be regarded as another prior art relevant to this invention. Unlike these prior arts, however, the present invention teaches us how to combine the related sciences and technologies associated with these arts in a system engineering sense so that any specific antigens or antibodies or antigenic neoplastic cells can be removed from blood or similar fluids with a high degree of specificity.

Further objects and advantages of the invention will become apparent from the study of the following portion of the specification, the claim, and the attached drawings.

NOTES

1.

a. D. Pressman, "Molecular Complementariness in Antigen-Antibody Systems", Molecular Structure and Biological Specificity, Ed. L. Pauling and H. A. Itano, American Institute of Biological Science, Washington, D.C.
b. L. Pauling, D. H. Campbell & D. Pressman, Physol. Rev., Vol. 23, pp 203-219, 1943.
2. G. R. Marrack, "The Chemistry of Antigens and Antibodies", Special Report Series, Medical Research Council, London, No. 230, 1938.
3.
a. M. Heidelberger, Bacteriol Rev., Vol. 3, p. 49, 1939.
b. J. H. Humphrey & R. G. White, *Immunology for Students of Medicine*, F. A. Davis Co., Phila, pp 198-199.
4.
a. M. Saito & H. P. Schwan, "The Time Constants of Pearl-Chain Formation", Proc. of Fort Ann, Tri-Serv. Conference on Biological Effects of Microwave Radiation, Vol. 1, pp 85-97, Plenum Press, N.Y., 1960.
b. L. D. Sher, "Technical Effects of AC Fields on Particles Dispersed in a Liquid", Biological Implications, ONR Tech. Report, No. 37, The Moore School of Electrical Engineering, Univ. of Penn, PA.
5. M. M. Burger, "A Difference in the Architecture of the Surface Membrane of Normal and Virally Transformed Cells", Proc. National Academy of Science, Vol. 62, 1969.

BRIEF DESCRIPTION OF THE DRAWINGS

FIG. 1 is a conceptual schematic arrangement of a biochemical filter which enables selective removal of specific biological cells from a fluid in a closed-loop fluid flowpath.

FIG. 2 is a simplified schematic arrangement for the removal of biological cells of relatively large dimensions.

DETAILED DESCRIPTION OF THE INVENTION

Figure 3:
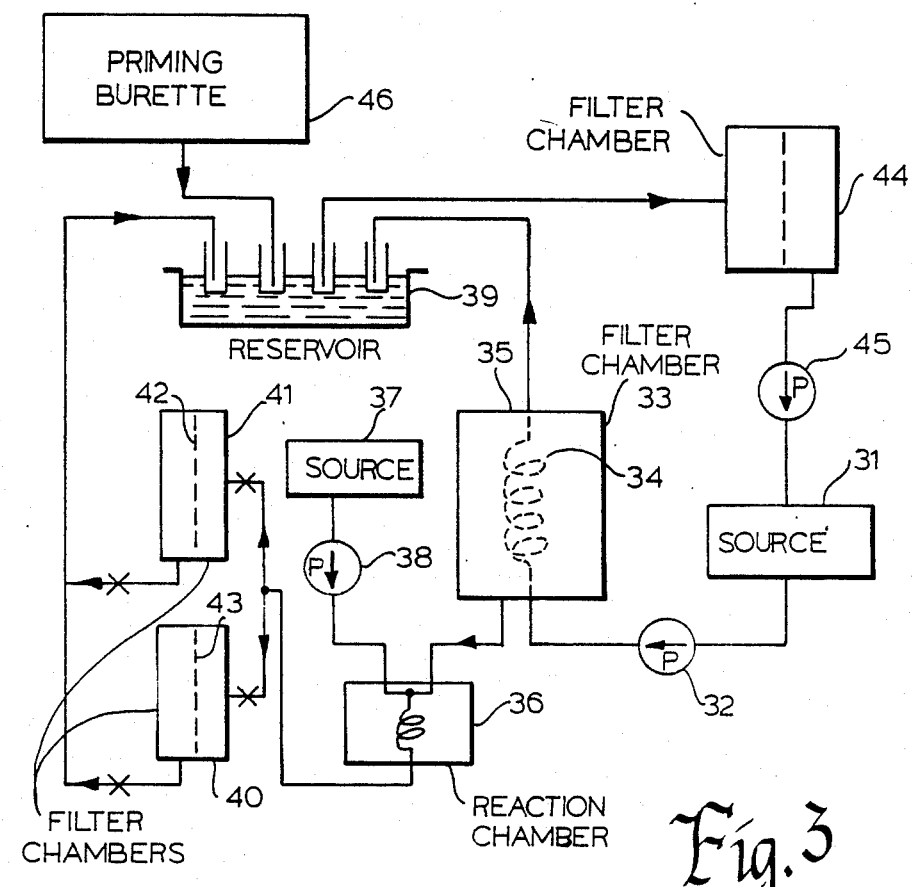
FIG. 3 is a simplified schematic arrangement for the removal of biological cells of relatively small dimensions.

FIG. 1 shows the conceptual arrangement for the selective removal of certain specific biological cells from a fluid. The first source, 1, embodies a mixture, in a fluid, of biological cells to be removed and other cells and particulates, which must remain unaffected by the cell removal process. This source is connected to a reaction chamber, 3, so that the fluid can flow into the reaction chamber at a controlled rate. The reaction chamber is also connected to a second source, 2, of complementary biological cells which react almost exclusively with the cells to be removed and form large clumps following the reaction. For example, the biological cells to be removed from the fluid are antigens, such as bacteria, viruses, fungi or parasites, the complementary cells will be corresponding antibodies or antisera which react almost exclusively with the particular type of antigens which are to be removed. Similarly, when the cells to be removed from the fluid are antibodies, the complementary cells will be specific antigens which will react almost exclusively with the antibodies to be removed. If the cells to be removed are virally transformed neoplastic cells, the complementary cells will be certain specific agglutinin which can agglutinate with the neoplastic cells but not with other cells including parent cells from which the neoplastic cells are derived.

The complementary cells are made to flow into the reaction chamber, also at a controlled rate. At the reaction chamber, clumps of biological cells to be removed and the complementary cells are formed, the dimensions of the clumps being considerably larger than other cells and particulates. The fluid containing the newly formed clumps and other unaffected cells and particulates is led to a filter chamber, 4, which retains the clumps as residue, because of the large dimensions of the clumps with respect to other cells and particulates, and permits the filtrate containing the fluid and unaffected cells and particulates to return to the first fluid source, 1. The filtering arrangement thus described, then, constitutes a closed-loop continuous fluid flow path. The biological cells which escape the reaction in one cycle are subjected to conditions favorable for the reaction over and over again in subsequent cycles. If the rate of removal of the cells is faster than their growth rate, the fluid eventually becomes free or almost free of such cells.

FIG. 2 illustrates, by way of an example, an embodiment of the invention where the dimension of the biological cells to be removed is comparable with the cells and particulates in the fluid which must remain unaffected by the cell removal process. In this arrangement, the source, 11, of the biological cells to be removed in a mixture with other cells and prticulates is connected to the reaction chamber, 13, through a pump, 12, a fluid rate control mechanism, which controls the rate of the flow of the fluid from the source, 11, to the reaction chamber 13. The source, 14, of the complementary biological cells which react almost exclusively with the cells to be removed is also connected to the reaction chamber, 13, through a pump, 15, a fluid rate control mechanism, which controls the flow rate of the complementary cells into the reaction chamber. Reactions of the cells to be removed and their complementary cells take place at the reaction chamber leading to the formation of clumps, the dimensions of which are many times larger than those of other cells and particulates in the fluid in source 11 or 14. The fluid, including the clumps and other cells and particulates unaffected by the reaction, is then led to the input side of a filter chamber, 16 or 17. Each filter chamber may consist of a membrane type partition, 18 or 19, which separates the input and output sides of the filter. The pore size of the membrane is so chosen that the large clumps are retained at the input side of the filter while the filtrate which does not contain any cell or particulate having a dimension more than about one third or one fourth of that of the pore size of the membrane, flows through the membrane to the output side of the filter chamber. The filtrate, then is led to a reservoir, 20, where it is storedtemporarily. Only one of the two filter chambers, 16 or 17, operates at any time. When the membrane in one filter is clogged up by the clumps, the fluid is channeled into the second filter without interrupting the closed-loop fluid flow path. After the second filter resumes its operation, the first filter chamber along with the clumps retained as residue are replaced by a new filter chamber. The process is repeated if the need exists. The rapidity with which the filter chamber needs replacement will depend on the concentration of the cells to be removed in the fluid.

Alternatively, the filter chamber may consist of a tube or similar container filled with glass beads of such dimensions and packing density as to retain the large clumps inside the filter chamber and allowing the filtrate with unaffected cells and particulates to flow through the tube and reach the reservoir, 20.

To illustrate the filtering action by way of an example, let it be assumed that the biological cells to be removed are some specific bacteria having an average diameter of 10 microns. Let the pore-size of the membrane in the filter be 40 microns, and the fluid is blood which contains other cells, such as the red and white cells and particulates, ranging in dimensions from 5 to 15 microns. When, as a result of the antigen-antibody reaction, clumps are formed and the minimum dimension of the clump is much bigger than 40 microns, the clumps will be retained by the filter while the blood with all its desired cells and particulates will flow through the filter as filtrate. Since the clumps will contain the bacteria, periodic replacement of the filter will cause the removal of the bacteria from the blood.

As shown in FIG. 2, an outlet of the reservoir, 20, is connected to another filter, 21, which will allow the fluid containing only the desired cells and particulates to pass through the filter, retaining any broken clumps which escape the first filter. The pore-size of the membrane, 22, used in the filter, 21, is smaller than the pore-size of the membrane 18 or 19, but larger than any desired cell or particulate in the fluid. The output of the filter 21 is connected to the first fluid source 11 through a pump 23, a fluid rate control mechanism the object of which is to regulate the flow of the fluid as it is reintroduced into the first fluid source. The reintroduction of the fluid into the first fluid source closes the fluid flow path loop.

A constant volume of fluid is usually maintained at the reservoir 20. To compensate for any loss of fluid during the filtering operation, a priming burette, 24, containing the same type of fluid as in source 11, but free of the undesired biological cells may be connected to the reservoir. In addition, an appropriate heat exchanger may be provided at the reservoir and at the reaction chamber. Also, a source of appropriate electromagnetic field to hasten clump formation may be introduced at the reaction chamber. Furthermore, bubble traps, 25, may be provided at convenient points in the closed-loop fluid flow path such as the filters and at the reservoir to make the system free of any undesired air.

FIG. 3 illustrates, by way of an example, another embodiment of the invention, where the dimensions of the biological cells to be removed from a fluid are significantly smaller than those of the cells and particulates which must remain unaffected during the cell-removal process. Here, the source, 31, embodies the fluid containing the biological cells to be removed along with other cells and particulates. This source is connected to a filter chamber, 33, through a pump, 32, the purpose of the pump being the regulation of the flow rate of the fluid to be processed. The filter chamber, 33, comprises a tube, 34, or a similar structure inside a fluid-tight enclosure, 35. The tube is made of a porous membrane which permits a part of the fluid containing all cells and particulates, having dimensions much smaller than those of the cells and particulates which should remain unaffected by the cell-removal process, to flow through it as the filtrate. The filtrate is collected in the enclosure, 35. The remaining fluid with larger cells and particulates than those in the filtrate is led to the reservoir, 39.

The filtrate collected in enclosure 35 is led to a reaction chamber, 36, which comprises a tube-like structure encased in a heat exchanger. The complementary biological cells which can react specifically with the cells to be removed are introduced in the reaction chamber, 36, from their source, 37, through a pump, 38, which controls the flow rate of the complementary cells into the reaction chamber.

Following the reaction in the reaction chamber, 36, clumps or agglutinates, containing the cells to be removed, are formed. The fluid containing the clumps and other non-reacted particles, if any, is then led to another filter chamber, 40 or 41. The clumps are retained at the membrane, 42 or 43, inside the filter chamber, 40 or 41, respectively, allowing the filtrate fluid to be collected at the reservoir, 39. Finally the fluid from the reservoir is returned to the source, 31, through another filter chamber, 44, and a pump, 45. The purpose of this filter is to prevent any cells, particulates or clumps, larger than those originally present in the fluid, to return to the source, 31. The purpose of the pump, 45, is to regulate the flow-rate of the returning fluid.

To further explain the operation of the cell-removal process in this case, let it be assumed that the cells to be removed are viruses, the dimensions of which are on the order of 0.1 micron. Let the fluid containing the viruses be blood which carries red and white cells and other particulates, the dimensions of which range from 5 to 15 microns. The porous tube, 34, in filter chamber 33 is so chosen that only the cells and particulates of dimensions less than 0.5 micron can flow through the pores into the enclosure 35. The contents of the enclosure, 35, then, will be the blood containing the viruses to be removed along with other cells and particulates, the dimensions of which are less than 0.5 micron. Such contents are then led to the reaction chamber, 36, where specific biological reactions take place among the viruses to be removed and the corresponding antibodies which are, in this case, the complementary biological cells introduced into the chamber from the antibody source, 37. If the pore-size of the membrane, 42 or 43, in the filter chamber, 40 or 41, is such that only cells and particulates of dimensions less than 0.5 micron can flow through it and if the minimum dimension of the clumps is greater than 1 micron, the filtrate of the filter chamber, 40 or 41, will be continuously freed from the viruses. If some viruses escape the reaction in one cycle, they will be subjected to conditions favorable for reaction over and over again until almost all the viruses are removed. As in FIG. 2, when one of the filter chambers, 40, for example, is filled with clumps, the fluid-flow is routed through filter chamber 41 without interrupting the continous fluid flow. Meanwhile, the filter chamber, 40, is replaced by a new one. This process is continued until all or most of the viruses are removed from the blood. Again, as in FIG. 2, a priming burette, 46, containing the same fluid as in the source, 31, is connected to the reservoir, 39, to compensate for any loss of fluid during the cell-removal process. Also, as in FIG. 2, the filter chamber, 44, prevents reentry into the source, 31, of any cells, particulates, or clumps, the dimensions of which are larger than 20 microns.

In a living system, where specific antigens or antibodies are to be removed from the blood, the sources 11 in FIG. 2 and 31 in FIG. 3, will be replaced by the blood circulatory system of the living body.

The above described embodiments and methods are furnished as illustrations of the principles of the invention and are not intended to define the only embodiments possible in accordance with the teachings of the invention. Rather, protection under the U.S. Patent Law shall be afforded to the inventor not only to the specific embodiments above, but to those falling within the spirit and terms of the invention as further defined in the following claims.

What is claimed is:

1. A biochemical filter system comprising;
   (a) a chamber containing specific biological cells to be separated in a fluid mixture of these cells, other biological cells and particulates;
   (b) a complementary source storage chamber containing corresponding complementary agglutinins which can react specifically with the biological cells to be separated to form clumps;
   (c) a reaction chamber, where specific reaction occurs, leading to the formation of clumps, said chamber having first and second inlets and and outlet;
   (d) means for connecting said chamber containing said biological cells to be separated to the first inlet of the reaction chamber and for introducing said specific biological cells into said reaction chamber;
   (e) means for connecting said chamber containing complementary agglutinins to the second inlet of the reaction chamber and for introducing said complementary agglutinins into said reaction chamber;
   (f) filter means coupled to said outlet of said reaction chamber for filtering the fluid containing the clumps and other cells and particulates following the reaction in the reaction chamber so as to retain the clumps as filter residue;
   (g) means for introducing the fluid containing the clumps and other cells and particulates following reaction in the reaction chamber into said filter means; and
   (h) means for returning the fluid filtrate following filtering to the chamber containing said biological cells.

2. A biochemical filter system as in claim 1, wherein said chamber contains specific antigens to be separated and said complementary source storage chamber contains corresponding complementary antibodies which react specifically to said antigens.

3. A biochemcical filter system as in claim 1, wherein said chamber contains biological cells with antigenic sites and said complementary source storage chamber contains corresponding antibodies having specific complementary sites and said reaction chamber promotes the biochemical reaction forming clumps.

4. A biochemical filter system as in claim 3, wherein the biological cells to be separated are leukemic leukocytes and the complementary antibodies comprise leukemic leukocyte antibodies.

5. A biochemical filter system as in claim 1, wherein the fluid is blood comprising plasma, red cells, leukocytes and other particulates not participating in said biochemical reaction.

6. A biochemical filter system as in claim 5, wherein the source of fluid is an in vivo blood circulatory system.

7. A biochemical filter system as in claim 1, wherein said chamber contains specific antibodies to be separated and said complementary source storage chamber contains corresponding complementary antigens which react specifically to said antibodies.

8. A biochemical filter system as in claim 1, wherein the fluid filtrate is returned to the chamber through a reservoir.

9. A biochemical filter system as in claim 1, wherein said system includes at least one pump in the fluidflow path between said chamber and the reaction chamber, between complementary source storage chamber and the reaction chamber, and in the path of the fluid filtrate returning means, to control the fluid flow rate therethrough, thereby to facilitate filtering of said specific biological cells to be removed from said fluid mixture.

10. A biochemical filter system as in claim 1, wherein the means for connecting the complementary source storage chamber to said reaction chamber includes a flow-rate control mechanism.

11. A biochemical filter system as in claim 1, wherein the filtering is effected by a membrane having pore dimensions larger than the dimensions of said specific biological cells, the complementary agglutinins, and other particulates in the fluid unaffected by the reaction but smaller than the dimensions of the clumps formed by said biological reaction.

12. A biochemical filter system as in claim 1, wherein the filtering is effected in a tube containing glass beads.

13. A biochemical filter system comprising:
   (a) a chamber containing specific antigens to be separated in a fluid mixture wherein the dimensions of said antigens are sufficiently smaller than most of the cells and particulates in the fluid mixture;
   (b) means for primary filtering the fluid mixture so that the primary filtrate comprises a portion of the fluid containing the specific antigens to be separated;
   (c) means for introducing said fluid mixture into said primary filtering means;
   (d) a complementary source storage chamber containing complementary antibodies specific to said antigens to be separated from said fluid;
   (e) a reaction chamber, where reaction between said antigens and antibodies occurs leading to the formation of clumps, said chamber having first and second inlets and an outlet;
   (f) means for conveying said primary filtrate into first inlet of the reaction chamber;
   (g) means for connecting said complementary source storage chamber to second inlet of the reaction chamber;
   (h) means connected to the oulet of said reaction chamber for secondary filtering of the fluid containing the clumps and other cells and particulates following the reaction in the reaction chamber so as to retain the clumps as filter-residue;
   (i) a reservoir with a plurality of inlets and an outlet;
   (j) means for connecting the fluid filtrate following secondary filtering to one inlet of the reservoir;
   (k) means for connecting the fluid filtrate following primary filtering to another inlet of the reservoir; and
   (l) means for returning the fluid accumulated at the reservoir to said fluid chamber containing antigens to be separated.

14. A biochemical filter system as in claim 13, wherein said chamber contains viruses to be separated from the fluid and said complementary source storage chamber contains antibodies specific to said viruses.

15. A biochemical filter system as in claim 13, wherein the fluid is blood comprising plasma, red cells, leukocytes and other prticulates non reactive with said complementary antibodies.

16. A biochemical filter system as in claim 13, wherein at least one pump is inserted into the fluid flow path to control the fluid flow rate.

17. A biochemical filter system as in claim 13, wherein the means for connecting the complementary source storage chamber includes a flow-rate control mechanism.

18. A biochemical filter system as in claim 13, wherein the secondary filtering is effected by a membrane having pore dimensions larger than the dimension of said specific antigens, the complementary antibodies and other particulates in the fluid unaffected by the reaction, but smaller than the dimensions of the clumps of reacted specific antigens and antibodies.

19. A biochemical filter system as in claim 13, wherein the source of fluid is an in vivo blood circulatory system.

20. A biochemical filter system as in claim 13, wherein the chamber contains specific antibodies to be separated, in a fluid mixture wherein the dimensions of said antibodies are sufficiently smaller than most of the cells and particulates in the fluid mixture and the complementary source storage chamber contains complementary antigens specific to said antibodies with means for primary filtering the fluid mixture so that the primary filtrate comprises a portion of the fluid containing the specific antibodies to be separated.

21. A method for selectively removing bacteria from an in vivo blood circulatory system which comprises:
  (a) guiding the blood containing the bacteria from an in vivo blood circulatory system to an external reaction chamber;
  (b) introducing complementary antibodies which can agglutinate with said bacteria into said reaction chamber;
  (c) allowing a bacteria-antibodies reaction to take place in said reaction chamber whereby clumps are formed of reacted bateria and complementary antibodies, said clumps having dimension filterably larger than those of the desired cells and particulates in the blood;
  (d) filtering out the clumps by passage of the blood through a filter; and
  (e) returning the filtered blood to the in vivo blood circulatory system.

22. A method for selectively removing viruses from an in vivo blood circulatory system, the dimensions of the viruses being smaller than other desired cells in the blood, which comprises:
  (a) diverting a portion of in vivo blood containing viruses from an in vivo blood circulatory system into an alternate path;
  (b) guiding the diverted blood containing viruses from the in vivo blood circulatory system to a primary filter which permits a portion of the diverted blood containing the viruses to be separated by filtration from the remaining portion of diverted blood containing larger cells and particulates and allowing the return of the diverted blood with larger cells and particulates to the in vivo blood circulatory system;
  (c) combining complementary antibodies with that portion of the blood containing the viruses whereby said viruses and complementary antibodies react and form clumps;
  (d) maintaining the reacted viruses and antibodies together to allow the forming of clumps of reacted viruses and antibodies, said clumps having dimensions filterably larger than the dimensions of the viruses to be removed;
  (e) filtering out the clumps by a secondary filter;
  (f) collecting the secondary filtrate without the clumps; and
  (g) returning the remaining diverted blood to the in vivo blood circulatory system.

23. A method of selectively removing specific biological cells, the dimensions of which are comparable to red and white cells, contained in a fluid mixture in an in vivo system which comprises:
  (a) diverting a portion of in vivo fluid containing the specific biological cells from the in vivo system into an alternate path;
  (b) introducing the diverted fluid containing said biological cells along with other cells and particulates present in the fluid into an external reaction chamber;
  (c) introducting complementary agglutinins which react with said biological cells to form clumps into said reaction chamber;
  (d) maintaining the specific biological cells and complementary agglutinins in said reaction chamber to allow a reaction to occur and the forming of clumps of reacted cells having dimensions filterably larger than other constituents of said fluid;
  (e) filtering out the clumps of reacted biological cells and agglutinins by a filter; and
  (f) returning the resulting filtrate without the clumps to the in vivo system.

24. A method for selectively removing specific antibodies, the dimensions of which are significantly smaller than the red and white cells in blood from an in vivo blood circulatory system which comprises:
  (a) diverting a portion of in vivo blood containing specific antibodies from a circulatory system into an alternate path;
  (b) introducing said diverted blood into a primary filter whereby the separation of that portion of diverted blood containing the antibodies to be removed from the remaining portion of diverted blood containing blood constituents which are filterably larger in dimension than the antibodies to be removed is performed;
  (c) conveying that portion of the blood with antibodies as detened following said primary filtering to a reaction chamber;
  (d) conveying the remaining blood containing red and white cells and other particulates following said primary filtering to a reservoir;
  (e) introducing into said reaction chamber complementary antigens which react with said antibodies to form clumps;
  (f) maintaining the specific antibodies and complementary antigens in said reaction chamber to allow an antigen-antibody reaction to occur and the formation of clumps having dimensions filterably larger than those of the antibodies to be removed by secondary filtration after discharge from said reaction chamber;
  (g) filtering out the clumps by a secondary filter; and
  (h) returning the secondary filtrate without clumps to the in vivo blood circulatory system.

25. The method as in claim 22 including storing the filtrate and the step of returning said secondary filtrate for reintroduction into said in vivo blood circulatory system.

26. A biochemical filter system for selectively separating certain specific biological materials selected from the group consisting of biological cells, antigens, antibodies, viruses, fungi and parasites, from a mixture of these materials and particulates in a fluid comprising:
- (a) a first storage chamber containing at least one of said group of specific biological materials in a fluid mixture;
- (b) a second storage chamber containing corresponding complementary biological materials which can react specifically with one of said group to be separated to form clumps;
- (c) a reaction chamber, where specific reaction occurs, leading to the formation of clumps, said chamber having first and second inlets and an outlet;
- (d) means for connecting said first storage chamber to the first inlet of the reaction chamber and for introducting one of said group into said reaction chamber;
- (e) means for connecting said second storage chamber to the second inlet of the reaction chamber and for introducing said complementary material into said reaction chamber;
- (f) filter means connected to said outlet of said reaction chamber for filtering the fluid containing the clumps and other substances and particulates following the reaction in the reaction chamber so as to retain the clumps as filter residue;
- (g) means for introducing the fluid containing the clumps and other materials and particulates following reaction in the reaction chamber into said filter means to produce a fluid filtrate; and
- (h) means for returning the fluid filtrate following filtering to the first storage chamber.

27. A biochemical filter system as in claim 26 wherein the biological materials to be separated are antigens and the complementary material which reacts with the biological materials to be seprated are antibodies specific to said antigens.

28. A biochemical filter system as in claim 26 wherein the biological materials to be separated are antibodies and the corresponding complementary biological materials are antigens.

* * * * *